United States Patent
Thomas-Soriot et al.

(10) Patent No.: US 11,389,650 B2
(45) Date of Patent: Jul. 19, 2022

(54) NEUROSTIMULATION METHOD FOR THE TREATMENT OF MODERATE TO SEVERE CHRONIC NOCICEPTIVE PAIN IN KNEE OSTEOARTHRITIS

(71) Applicant: SUBLIMED, Moirans (FR)

(72) Inventors: Sandrine Thomas-Soriot, Amiens (FR); Patricia Abraham-Briffod, Grenoble (FR); Florent Le Bastard, St. Egreve (FR)

(73) Assignee: SUBLIMED, Moirans (FR)

( * ) Notice: Subject to any disclaimer, the term of this patent is extended or adjusted under 35 U.S.C. 154(b) by 586 days.

(21) Appl. No.: 16/186,264

(22) Filed: Nov. 9, 2018

(65) Prior Publication Data

US 2020/0147378 A1    May 14, 2020

(51) Int. Cl.
    *A61N 1/36*    (2006.01)
    *A61N 1/04*    (2006.01)

(52) U.S. Cl.
    CPC ......... *A61N 1/36021* (2013.01); *A61N 1/048* (2013.01); *A61N 1/0452* (2013.01); *A61N 1/0456* (2013.01); *A61N 1/0492* (2013.01)

(58) Field of Classification Search
    CPC .............. A61N 1/36021; A61N 1/0452; A61N 1/0456; A61N 1/048; A61N 1/0492
    See application file for complete search history.

(56) References Cited

U.S. PATENT DOCUMENTS

| | | | |
|---|---|---|---|
| 9,775,662 B2 | 10/2017 | Ingvarsson et al. | |
| 2006/0064139 A1* | 3/2006 | Chung | A61M 21/00 607/45 |
| 2009/0319003 A1* | 12/2009 | Castel | A61N 1/36031 607/48 |
| 2013/0085317 A1* | 4/2013 | Feinstein | A61N 1/36021 600/14 |
| 2014/0276539 A1* | 9/2014 | Allison | A61F 7/12 604/500 |
| 2014/0343543 A1* | 11/2014 | Karnik | A61F 7/12 606/24 |
| 2017/0095656 A1 | 4/2017 | Perraud et al. | |
| 2017/0136228 A1 | 5/2017 | Perraud et al. | |
| 2017/0136229 A1 | 5/2017 | Karst et al. | |
| 2017/0151427 A1 | 6/2017 | Perraud et al. | |

* cited by examiner

*Primary Examiner* — Catherine M Voorhees
*Assistant Examiner* — Roland Dinga
(74) *Attorney, Agent, or Firm* — Hauptman Ham, LLP

(57) ABSTRACT

A method for treating chronic nociceptive pain of knee osteoarthritis comprising the steps of: placing a first set of electrodes in contact with the skin on the inner side of the knee on the path of the infrapatellar nerve; and generating a first electrical signal with a signal generator and applying said first signal to the first set of electrodes so as to produce external, i.e. non invasive, electrostimulation of the infrapatellar nerve of the knee.

13 Claims, 3 Drawing Sheets

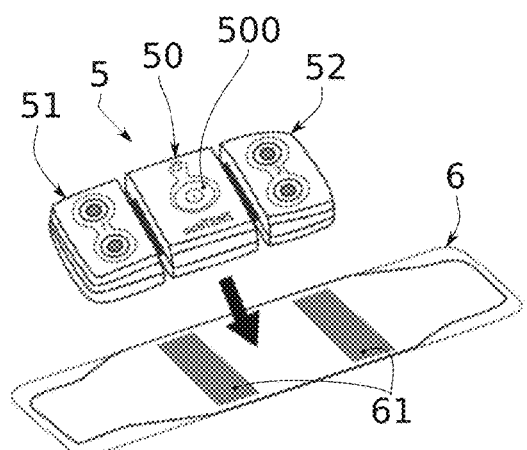
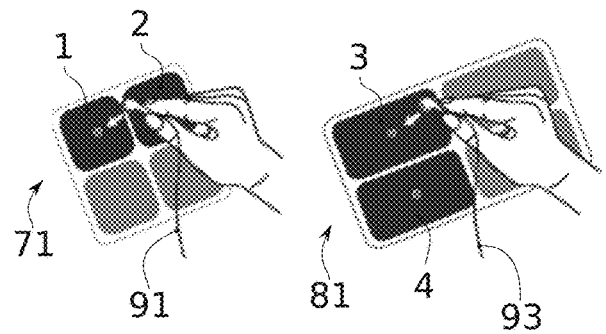
Fig. 2A   Fig. 2B
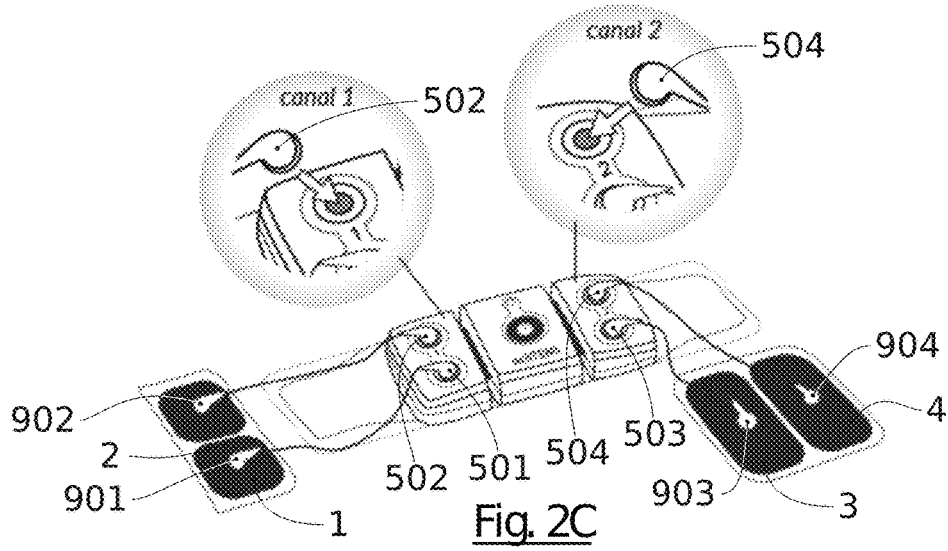
Fig. 2C
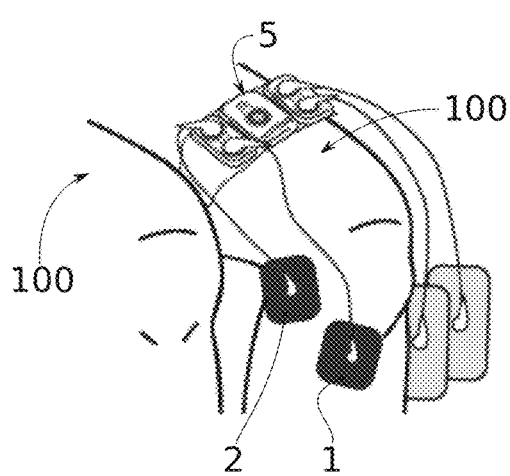
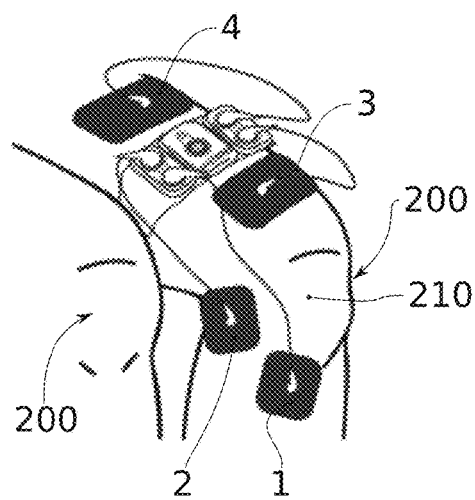
Fig. 3A   Fig. 3B

NEUROSTIMULATION METHOD FOR THE TREATMENT OF MODERATE TO SEVERE CHRONIC NOCICEPTIVE PAIN IN KNEE OSTEOARTHRITIS

CROSS-REFERENCE TO RELATED PATENT APPLICATIONS

The entire teachings and disclosure of each of the applications mentioned below are incorporated by reference in this patent application under 37 CFR 1.57, and are expressly considered hereby as a part of it:
U.S. Patent Application No. 2017/0136228 A1,
U.S. Patent Application No. 2017/0136229 A1,
U.S. Patent Application No. 2017/0151427 A1,
U.S. Patent Application No. 2017/0095656 A1.

FIELD

One or more embodiments pertain to the field of Transcutaneous Electrical Nerve Stimulation, more commonly called TENS. One or more embodiments are useful for treating chronic pain due to Knee OsteoArthritis (KOA).

BACKGROUND

Osteoarthritis (OA) is a debilitating chronic condition requiring long-term treatment of pain and inducing functional impairment. More specifically knee osteoarthritis (KOA) is a common disease associated with significant morbidity. It is one of the leading causes of global disability. Its prevalence increases with age and/or obesity dramatically. KOA is frequently associated with pain which can worsen with daily activities. The goals of KOA treatments are to provide pain relief and to improve function and quality of life.

Drug therapies comprising systemic step 2 analgesics are generally used to treat chronic, nociceptive pain in patient suffering from KOA.

However, such treatments are associated with drug side effects and tolerance leading sometimes to addiction, according to the American college of Rheumatology. In order to address these issues, a non-drug treatment that can relieve pain of a patient suffering from KOA, without side effects, would be of great advantage.

Electrostimulation is a technique allowing muscle activation and/or pain blocking.

Such a technique has been considered for rehabilitation of patient suffering from KOA.

U.S. Pat. No. 9,775,662 B2 reports an osteoarthritis knee brace comprising an electrical stimulation system. This system may comprise electrodes and sensors configured to detect and to analyze motion during gait and to activate muscle groups so as to correct muscle activity during gait. This brace is mainly orthopedic.

Such a brace has significant costs. It is also uneasy to suit and to use for patients.

One or more embodiments of the present disclosure aim at finding a non-drug method for treating chronic nociceptive pain of knee osteoarthritis (KOA).

Additionally, one or more embodiments of the present disclosure aim at providing an easy and cost effective method for patients suffering from KOA.

SUMMARY

The present invention relates to a method for treating chronic nociceptive pain of knee osteoarthritis comprising the steps of:

placing a first set of electrodes in contact with the skin on the inner side of the knee on the path of the infrapatellar nerve;

generating a first electrical signal with a signal generator and applying said first signal to the first set of electrodes so as to produce external, i.e. non invasive, electrostimulation of the infrapatellar nerve of the knee.

The method according to one or more embodiments is particularly suitable to implement Transcutaneous Electrical Nerve Stimulation, more commonly referred to as TENS.

TENS activates a complex neural network and could result in a reduction in pain intensity under specific conditions.

To reach these conditions and to optimize TENS efficiency for pain reduction in KOA diseases, the method according to one or more embodiments involves placing the electrodes on the path of the infrapatellar nerve, on the inner side of the knee and/or on the inner side of the thigh.

The infrapatellar nerve is a branch of the saphenous nerve and is intended for the innervation of a subrotulian region, which is particularly stressed in case of KOA disease. The infrapatellar nerve is the nerve branch covering the largest part of the knee, in particular the antero-internal part of the knee. It is mainly responsible for knee nociception. The infrapatellar nerve, which is a branch of the saphenous nerve, which is a branch of the femoral nerve, ultimately has roots at the level of the L2, L3, L4 vertebrae.

Such a placement of the electrodes thus allows the excitation of the infrapatellar nerve, resulting in turn in pain relief for patients suffering from KOA at moderate to severe pain intensities.

The method according to one or more embodiments may further comprise one or a suitable combination of the following characteristics:

The first set of electrodes comprises a first electrode and a second electrode, and the placement of said first set of electrodes comprises the steps of:

placing the first electrode in a first region of the inner side of the knee, next to the subrotulian skin triangle, preferably under the medial epicondyle of the femur, and preferably above the medial patellar retinaculum, and preferably in front of the tendon of the semimembranosus muscle;

placing the second electrode in a second region of the inner side of the thigh, next to the first electrode, on the path of the saphenous nerve, preferably right above the medial epicondyle of the femur, and preferably above the medial patellar retinaculum, and preferably behind the tendon of the large abductor muscle.

The method according to an embodiment may further comprise the steps of:

placing a second set of electrodes in contact with the skin on the anterior face of the thigh, on the path of the quadriceps muscle;

generating a second electrical signal with the signal generator and applying said second signal to the second set of electrodes so as to produce external, i.e. non invasive, electrostimulation of the quadriceps muscle.

The second set of electrodes comprises a third electrode and a fourth electrode, and the placement of said second set of electrodes comprising the steps of:

placing the third electrode in a third region of tendonmuscular junction between the kneecap and the quadriceps muscle, preferably on the anterior quadriceps head;

placing the fourth electrode in a fourth region opposite to the third region, preferentially on the middle of the quadriceps, preferably at least on the rectus femoris of the quadriceps muscle.

The signal generator is portable, and preferably flexible, and the method comprises the step of:

fixing said portable signal generator on the thigh in the vicinity of first set of electrodes, or fixing said portable signal generator on the thigh in the vicinity of first and second set of electrodes.

The portable signal generator is controllable wirelessly.

The first electrical signal is pulsed and has an impulse frequency between 80 and 100 Hz, a pulse width in the range 150 µs to 200 µs and a current intensity between 1 and 60 mA.

The second electrical signal is pulsed and has an impulse frequency between 1 and 5 Hz, a pulse width in the range 200 µs to 250 µs and a current intensity between 1 and 25 mA.

The first and second electrodes have a surface area in the range 8 cm$^2$ to 40 cm$^2$, so as to cover the afferent path of the infrapatellar nerve, and/or the path of the saphenous nerve. These first and second electrodes can thus be easily placed to excite the infrapatellar nerve and/or the saphenous nerve.

The third and fourth electrodes have a surface area in the range 40 cm$^2$ to 110 cm$^2$. The third and fourth electrodes can thus be easily placed to stimulate the quadriceps muscle.

BRIEF DESCRIPTION OF THE DRAWINGS

FIG. 2A shows a step of fastening the signal generator to an adhesive support, according to an embodiment of the invention.

FIG. 2B shows a step of connecting electrical cables to electrodes respectively of first and second sets of electrodes, according to an embodiment of the invention.

FIG. 2C shows a step of connecting electrical cables coming from first and second sets of electrodes respectively to first and second channels of the signal generator, according to an embodiment of the invention.

FIG. 3A shows a step of placing first and second electrodes respectively in a first region of the inner side of the knee, next to the subrotulian skin triangle, and in a second region of the inner side of the thigh, according to an embodiment of the invention.

FIG. 3B shows a step of placing third and fourth electrodes respectively in a third region of tendon-muscular junction between the kneecap and the quadriceps, and in a fourth region opposite to the third region, on the quadriceps, according to an embodiment of the invention.

DETAILED DESCRIPTION

Figure 1:
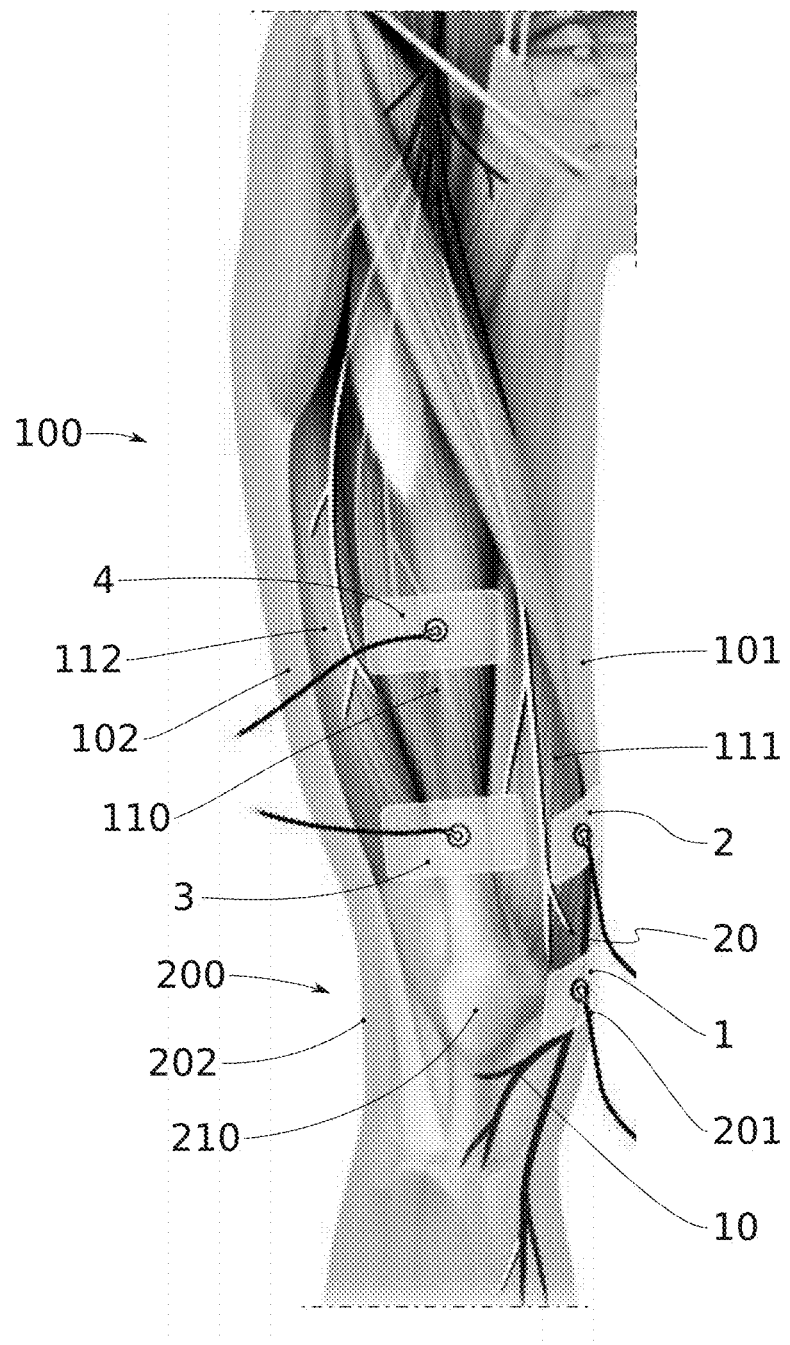
FIG. 1 schematically represents thigh and knee anatomy along with the placement of first and second electrodes on the path of the infrapatellar nerve, and the placement of third and fourth electrodes on the quadriceps, according to an embodiment of the invention.

As illustrated in FIG. 1 for the sake of clarity, thigh 100 has an inner side 101, an outer side 102 opposite to the inner side 101, an anterior face and a posterior face opposite to the anterior face.

The inner side of the right thigh is facing the inner side of the left thigh.

The quadriceps muscles, comprising rectus femoris 110, vastus medialis 111, vastus intermedius (not visible) and vastus lateralis 112, are on the side of the thigh anterior face.

Knee 200 has an inner side 201, an outer side 202 opposite to the inner side 201, an anterior face and a posterior face opposite to the anterior face.

Kneecap 210 is on the side of the knee anterior face.

Nociception covers all phenomena that allow a painful stimulus to be transmitted to the central nervous system via the activation of cutaneous, muscular and/or joint nociceptors (pain receptors).

As discussed herein, electrical stimulation is preferably of the type commonly referred to as Transcutaneous Electrical Nerve Stimulation (TENS) used primarily for pain alleviation. It involves transmitting low-intensity electric pulses near the area of pain via electrodes placed on the skin of a patient.

Two main action mechanisms are involved in TENS:

A first mechanism known as "Gate Control" is based on the principle of inhibiting the pain signal. While TENS is being used, this signal is replaced by a prickling sensation for the patient. This sensation short-circuits the pain signal at the level of the spinal cord and prevents it from reaching the brain.

Gate control is preferably obtained using high frequency electrical signals (80 to 100 Hz). It is the main mechanism of the so-called high frequency mode of TENS (HF-TENS), or conventional mode of TENS (C-TENS).

A second mechanism referred to as "Endorphinic Stimulation" favors an increase in the production of endorphins, resulting in an overall analgesic effect.

The endorphinic stimulation is characterized by a sensation of small beats for the patient. Endorphinic stimulation acts at supraspinal level, typically at muscle level. It allows a release, at the medullary level, of endogenous opioid substances by stimulating muscle fibers. Endorphinic stimulation is preferably obtained using low frequency electrical signals (1 to 5 Hz). It is the main mechanism of the so-called low frequency mode of TENS (LF-TENS), or Acupuncture Like mode of TENS (AL-TENS).

Endorphinic stimulation may be obtained by stimulating any muscle, especially any muscle of the thigh, that has its nerve roots between the vertebrae L2 to L5.

In one or more embodiments of the present invention, it is for instance possible to create endorphins by stimulating a muscle of the right thigh to alleviate pain due to KOA in the left thigh.

In one or more embodiments of the present invention, the muscles which are preferably stimulated are:

The rectus femoris (innerved by the femoral nerve);

The vastus medialis (innerved by the vastus medialis nerve);

The vastus intermedius (innerved by the vastus intermedius nerve and a branch of the vastus lateralis nerve);

The vastus lateralis (innerved by the vastus lateralis nerve).

The pain caused by KOA triggers reflex contracture on the quadriceps. The muscle stimulation first relax the muscle and subsequently reduce contracture. Then the muscle stimulation leads to endorphin generation at least after 30 minutes of muscle stimulation.

As a consequence, AL-TENS in one or more embodiments of the present invention is preferably applied for more than 30 minutes.

For convenience, electrostimulation refers herein to C-TENS and/or AL-TENS, with the recognition that the type of stimulation may be one or other of the above action mechanisms or a combination of both.

According to one or more embodiments of the present invention, the objective of reducing pain in case of KOA disease is specifically achieved by external electrostimulation of the infrapatellar nerve 10, which is a branch of the saphenous nerve 20 (see FIG. 1).

Figure 5:
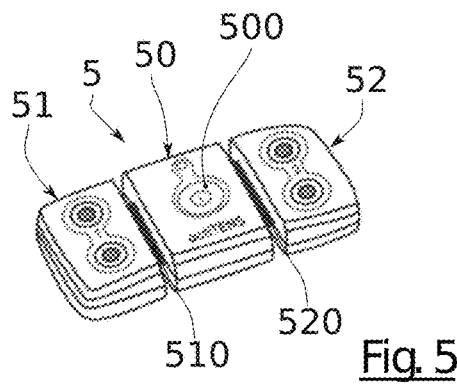
FIG. 5 represents a more detailed view of a portable signal generator according to a preferred embodiment, reducing constructively the invention to practice.
Figure 6:
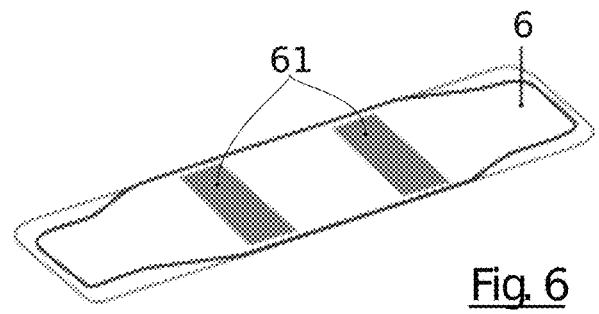
FIG. 6 represents a more detailed view of an adhesive support according to a preferred embodiment, reducing constructively the invention to practice.

The method may be carried out with a portable signal generator (see FIG. 5) fasten on an adhesive support, said support being removably stuck on the thigh, said generator 5 having at least a first channel 51 and a second channel 52, and a central unit 50.

The first channel 51 is preferably designed to be connected to a first set of electrodes and the second channel 52 is preferably designed to be connected to a second set of electrodes.

The central unit 50 may be designed to receive command signals from a remote control unit, typically a smartphone, and to deliver first and/or second electrical signals respectively to first and/or second channels.

The first and second channels can be controlled independently.

The central unit 50 is preferably located between the first and second channels 51, 52. The central unit 50 may be connected to the first channel 51 via a first flexible connection or hinge 510. The central unit 50 may be connected to the second channel 52 via a second flexible connection or hinge 520. Such a generator 5 is then articulated and may advantageously conform to the shape of the thigh. Overall ergonomics of the generator are thus improved. The generator is then easy to suit and the method is easy to use for patients.

Such a compact and connected generator 5 has been developed and is available from Sublimed Company, as actiTENS model.

According to at least one embodiment, the actiTENS signal generator 5 is fixed on an adhesive support 6 by scratches 61, as illustrated in FIG. 2A.

Figure 8A:
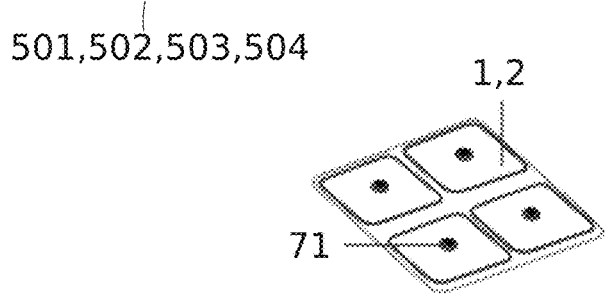
FIG. 8A to 8D represent more detailed views of sets of electrodes according to different embodiments of the electrodes, reducing constructively the invention to practice.
Figure 8B:
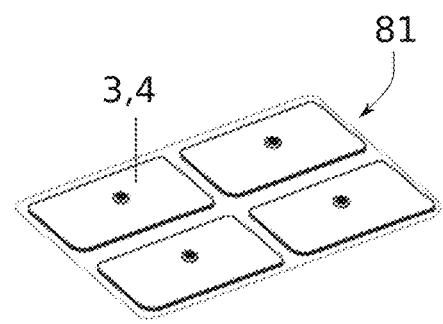
Figure 8C:
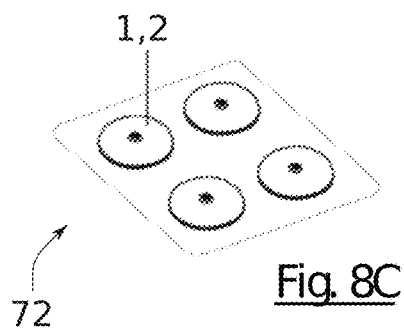

The first set 71 of electrodes is preferably chosen among sets 71, 72 of so-called small electrodes illustrated in FIG. 8A, 8C.

Such so-called small electrodes may present a surface area in the range 8 cm$^2$ to 30 cm$^2$, typically about 20 cm$^2$ or 25 cm$^2$. They may have a square shape, or a round shape, or other suitable shapes. The size of the small electrodes is chosen according to the patient morphology, so as to cover the different branches of infrapatellar nerve 10 and/or saphenous nerve 20.

A first electrode 1 and a second electrode 2 of the first set 71 are respectively connected via electrode connectors to first and second electrical cables 91, 92, as illustrated in FIG. 2B.

Figure 8D:
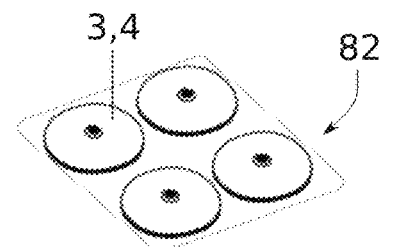

The second set 81 of electrodes is preferably chosen among sets 81, 82 of so-called large electrodes illustrated in FIG. 8B, 8D.

Such so-called large electrodes may present a surface area in the range 40 cm$^2$ to 60 cm$^2$ up to 100 cm$^2$, typically about 45 cm$^2$. They may have a rectangular shape, or a round shape, or other suitable shapes. The size of the large electrodes is chosen according to the patient morphology, so as to cover a part of the rectus femoris 110, and/or a part of the vastus medialis 111 and/or a part of the vastus lateralis 112.

A third electrode 3 and a fourth electrode 4 of the second set 81 are respectively connected via electrode connectors to third and fourth electrical cables 93, 94, as illustrated in FIG. 2B.

Electrical cables 91, 92, 93, 94 are used to connect electrodes 1, 2, 3, 4 to the signal generator 5 via generator connectors as illustrated in FIG. 2C.

Electrode connectors 901, 902, 903, 904 and generator connectors 501, 502, 503, 504 respectively on both ends of electrical cables 91, 92, 93, 94, may be clip-on tips to facilitate the connections.

Electrode connectors and generator connectors are preferably unlike, for instance by means of a failsafe.

In particular, electrode connectors may exhibit a fine clip-on tip to reduce the overall space requirement for electrodes. Advantageously, electrode connectors have a fine clip-on tip to reduce the weight of the corresponding electrodes placed on the painful area. They may have a magnetic system of fixation as described in the U.S. Patent Application No. 2017/0095656 A1.

Figure 7:
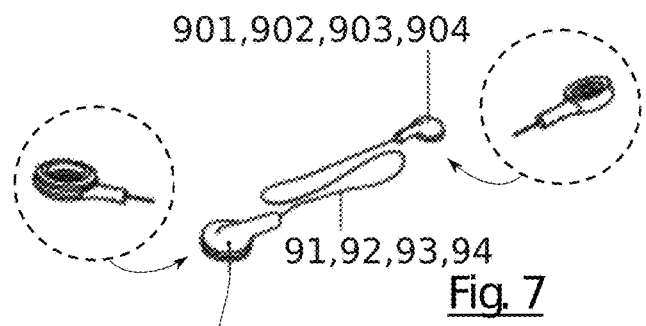
FIG. 7 represents a more detailed view of an electrical cable along with electrical connectors at its ends, according to a preferred embodiment, reducing constructively the invention to practice.

Generator connectors may exhibit a thick clip-on tip to strengthen the connection to generator 5, as illustrated in FIG. 7. Such generator connectors allow for instance an IP 22 degree of protection, in accordance with code from International Protection Marking.

Alternatively, electrode connectors and generator connectors may be similar for simplicity.

Electrical cables 91, 92, 93, 94 can exhibit different lengths, for example a "short" length between 5 cm and 15 cm, typically about 14 cm, a "medium" length between 20 cm and 50 cm, typically about 40 cm, and a "long" length between 50 cm and 120 cm, typically about 100 cm.

Four short length electrical cables 91, 92, 93, 94 may be used for instance to connect the four electrodes 1, 2, 3, 4 to the signal generator 5, depending on the relative locations of electrodes 1, 2, 3, 4 and signal generator 5.

First and second electrodes 1, 2 are preferably connected to the first channel 51 of the signal generator 5.

Third and fourth electrodes 3, 4 are preferably connected to the second channel 52 of the signal generator 5.

The generator 5 is positioned onto the thigh 100, preferably on the anterior face of the thigh 100, roughly at a centered transverse position relatively to the thigh 100.

The generator 5 is preferably fixed onto the thigh 100 via the adhesive support 6.

The signal generator 5 may be positioned and fixed on the thigh 100 before clipping the generator connectors or after clipping the generator connectors.

The signal generator 5 may be positioned and fixed on the thigh 100 before positioning electrodes or after positioning electrodes.

At least one embodiment of the invention is as follows:

The first electrode 1 is positioned on the inner side 201 of the knee 200, next to the subrotulian skin triangle, on the path of the infrapatellar nerve 10 as illustrated in FIGS. 1 and 3A. The first electrode 1 is preferably positioned under the medial epicondyle of the femur, and preferably above the medial patellar retinaculum, and preferably in front of the tendon of the semimembranosus muscle. It allows an optimized stimulation of the branches of the infrapatellar nerve 10.

The second electrode 2 is positioned on the inner side 201 of the knee 200 or on the inner side 101 of the thigh 100, next to the first electrode 1, on the path of the saphenous nerve 20 as illustrated in FIGS. 1 and 3A. The second electrode 2 is preferably positioned right above the medial epicondyle of the femur, and preferably above the medial patellar retinaculum, and preferably behind the tendon of the large abductor muscle. It allows an optimized stimulation of the saphenous nerve 20.

The third electrode 3 is positioned on the anterior face of the thigh 100, at the tendon-muscular junction between the kneecap 210 and the quadriceps 110, 111, 112, preferably at a centered transverse position relatively to the rectus femoris 110 as illustrated in FIGS. 1 and 3B. The third electrode 3 is preferably positioned on the anterior quadriceps head.

The fourth electrode 4 is positioned on the anterior face of the thigh 100, preferably at a transverse position relatively to the thigh 100, such as the electrodes 3, 4 are on either side of the generator 5 as illustrated in FIGS. 1 and 3B. The fourth electrode 4 is preferably positioned on the middle of the quadriceps, preferably on the rectus femoris 110, and preferably at least partially on the vastus medialis 111 and/or the vastus lateralis 112. The quadriceps muscle is the biggest muscle of the thigh and has the most sensitive fibers. Such a placement thus allows an optimized stimulation for endorphins release.

After positioning each electrodes 1, 2, 3, 4 and the signal generator 5, an electrostimulation session can be started.

According to at least one embodiment of the invention, the patient can directly control the signal generator 5 via its smartphone and a dedicated app.

After switching on the generator via the start button 500, the patient can choose between several types of electrostimulation programs involving the first set of electrodes and/or the second set of electrodes.

The first electrical signal is applied to the first set of electrodes via the first channel 51 of the signal generator 5.

The second electrical signal is applied to the second set of electrodes via the second channel 52 of the signal generator 5.

The intensity of first and/or second electrical signals can be set up independently.

The first electrical signal may have an intensity in the range 1 mA to 60 mA, for instance about 8 mA, a frequency in the range 80 Hz to 120 Hz, for instance about 100 Hz, and a pulse width in the range 150 µs to 250 µs, for instance about 200 µs. This allows gate control mechanism involved in C-TENS electrostimulation.

The second electrical signal may have an intensity in the range 1 mA to 60 mA, for instance about 12 mA, a frequency in the range 1 Hz to 5 Hz for instance about 2 Hz, and a pulse width in the range 200 µs to 300 µs, for instance about 250 µs. This allows endorphinic stimulation mechanism involved in AL-TENS electrostimulation.

The adjustment of intensities and/or frequencies and/or pulse widths may depend on the type of electrostimulation desired, or on a medical prescription, or on the patient's feeling.

The method is implemented with a mixed program comprising a first electrical signal on the first channel corresponding to a gate control mechanism and a second electrical signal on the second channel corresponding to an endorphinic stimulation mechanism. In this case, pulse widths of first and second electrical signals may be the same.

Typically, the first electrical signal intensity and/or the second electrical signal intensity are set up at a sustainable level for the patient so that the patient's feeling is not painful.

The electrostimulation session duration is preferably set between 10 min and 2 hours, preferably between 30 min and 1.5 hours.

The data concerning the electrostimulation session can be saved, for instance for a fast program recall in order to perform daily sessions.

The method described herein allows advantageously a pain relief in KOA disease.

While the foregoing embodiments have been described and shown, alternatives and modifications of these embodiments may be made to fall within the scope of the disclosure. The principles described may be implemented with other types of signal generators. For instance, first and second channels may be connected to a common reference electrode and respectively to a C-TENS electrode and a AL-TENS electrode, so that first and second signals are applied respectively between the C-TENS electrode and the reference electrode, and between the AL-TENS electrode and the reference electrode.

What is claimed is:

1. A method of treating chronic nociceptive pain of knee osteoarthritis comprising the steps of:
   placing a first set of electrodes in contact with the skin on the inner side of the knee on the path of the infrapatellar nerve;
   generating a first electrical signal with a signal generator and applying said first signal to the first set of electrodes so as to produce external electrostimulation of the infrapatellar nerve of the knee;
   placing a second set of electrodes in contact with the skin on the anterior face of the thigh; and
   generating a second electrical signal with the signal generator and applying said second signal to the second set of electrodes so as to produce external electrostimulation of the quadriceps muscle,
   wherein
   the first electrical signal is pulsed and has an impulse frequency between 80 and 100 Hz, a pulse width in the range 150 µs to 200 µs and a current intensity between 1 and 60 mA, and
   the second electrical signal is pulsed and has an impulse frequency between 1 and 5 Hz, a pulse width in the range 200 µs to 250 µs and a current intensity between 1 and 60 mA.

2. The method according to the claim 1, wherein the first set of electrodes comprises a first electrode and a second electrode, the placement of said first set of electrodes comprising the steps of:
   placing the first electrode in a first region of the inner side of the knee, next to the subrotulian skin triangle; and
   placing the second electrode in a second region of the inner side of the thigh, next to the first electrode, on the path of the saphenous nerve.

3. The method according to claim 2, wherein the first and second electrodes has a surface area in the range 8 cm$^2$ to 40 cm$^2$, so as to cover the afferent path of the infrapatellar nerve, and/or the path of the saphenous nerve.

4. The method according to claim 1, wherein the second set of electrodes comprises a third electrode and a fourth electrode, the placement of said second set of electrodes comprising the steps of:
   placing the third electrode in a third region of tendon-muscular junction between the kneecap and the quadriceps; and
   placing the fourth electrode in a fourth region opposite to the third region, on the rectus femoris of the quadriceps.

5. The method according to claim 4, wherein the third and fourth electrodes have a surface area in the range 40 cm$^2$ to 110 cm$^2$.

6. The method according to claim 1, wherein the signal generator is portable, said method comprising the step of:
fixing said portable signal generator on the thigh in the vicinity of the first set of electrodes.

7. The method according to claim 6, wherein the portable signal generator is controllable wirelessly.

8. The method according to claim 1, wherein the signal generator is portable, said method comprising the step of:
fixing said portable signal generator on the thigh in the vicinity of first and second sets of electrodes.

9. The method according to claim 1, wherein said placing the first set of electrodes includes placing an electrode in contact with the skin on the inner side of the knee on the path of the infrapatellar nerve and adjacent to the kneecap of the knee.

10. The method according to claim 1, further comprising fixing the signal generator on the thigh via an adhesive support.

11. A method of treating chronic nociceptive pain of knee osteoarthritis, the method comprising:
placing a first set of electrodes in contact with a skin on an inner side of a knee on a path of an infrapatellar nerve, the first set of electrodes including a first electrode and a second electrode;
generating a first electrical signal with a signal generator and applying said first electrical signal to the first set of electrodes so as to produce external electrostimulation of the infrapatellar nerve of the knee;
placing a second set of electrodes in contact with the skin on an anterior face of a thigh, the second set of electrodes including a third electrode and a fourth electrode; and
generating a second electrical signal with the signal generator and applying said second electrical signal to the second set of electrodes so as to produce external electrostimulation of a quadriceps muscle,
wherein
the placing of said first set of electrodes includes:
placing the first electrode in a first region of the inner side of the knee, next to a subrotulian skin triangle; and
placing the second electrode in a second region of an inner side of the thigh, next to the first electrode, on a path of a saphenous nerve,
the placing of said second set of electrodes includes:
placing the third electrode in a third region of tendon-muscular junction between a kneecap and a quadriceps; and
placing the fourth electrode in a fourth region opposite to the third region, on a rectus femoris of the quadriceps, and
the first electrode is placed in contact with the skin on the inner side of the knee on the path of the infrapatellar nerve and adjacent to the kneecap of the knee.

12. The method according to claim 11, wherein the first electrical signal is pulsed and has an impulse frequency between 80 and 100 Hz, a pulse width in the range 150 μs to 200 μs and a current intensity between 1 and 60 mA.

13. The method according to claim 12, wherein the second electrical signal is pulsed and has an impulse frequency between 1 and 5 Hz, a pulse width in the range 200 μs to 250 μs and a current intensity between 1 and 60 mA.

* * * * *